United States Patent [19]

Hanausek-Walaszek et al.

[11] Patent Number: 5,411,868
[45] Date of Patent: * May 2, 1995

[54] DIAGNOSTIC AND PREMONITORING USES OF A 65 KDA TUMOR-ASSOCIATED PROTEIN IN COMPANION AND DOMESTIC ANIMAL MALIGNANCY

[75] Inventors: Margaret Hanausek-Walaszek; Lezlee Coghlan, both of Bastrop, Tex.

[73] Assignee: Board of Regents, The University of Texas System, Austin, Tex.

[*] Notice: The portion of the term of this patent subsequent to May 10, 2011 has been disclaimed.

[21] Appl. No.: 21,738

[22] Filed: Feb. 23, 1993

Related U.S. Application Data

[63] Continuation of Ser. No. 460,045, Jan. 2, 1990, which is a continuation-in-part of Ser. No. 426,408, Oct. 24, 1989.

[51] Int. Cl.⁶ ............... G01N 33/543; G01N 33/531; G01N 33/53; C07K 15/06
[52] U.S. Cl. ............................ 435/7.23; 435/7.95; 530/358; 530/388.8; 530/387.7; 530/389.7
[58] Field of Search ............... 435/7.23, 7.95; 530/358, 388.8, 387.7, 389.7

[56] References Cited

U.S. PATENT DOCUMENTS

| | | | |
|---|---|---|---|
| 4,368,262 | 1/1983 | Bucovaz | 435/23 |
| 4,448,890 | 5/1984 | Smetana | 436/508 |
| 4,707,438 | 11/1987 | Keydar | 435/5 |
| 4,746,539 | 5/1988 | Webb | 424/85 |
| 4,775,620 | 10/1988 | Cardiff | 435/7 |

(List continued on next page.)

OTHER PUBLICATIONS

Nilsson et al., "Immunization of Mice and Rabbits by Intrasplenic Deposition of Nanogram Quantities of Protein Attached to Sepharose Beads or Nitrocellulose Paper Strips", J. Immunol. Meth. 99 (1987) 67–75.

Langor, R. "Polymers for the Sustained Release of Macromolecules: Their Use in a Single-Step Method of Immunization," in Meth Enz 73, 57–75 (1981).

Hanausek-Walaszek et al., Cancer Letters, 33:55–61 (1986).

Hanausek-Walaszek et al., Journal of Medicine, 17:13–23 (1986).

Hanausek-Walaszek et al., Biochemical and Biophysical Research Communications, 127:779–785 (1985).

Hanausek-Walaszek et al., Carcinogenesis, 6:1725–1730 (1985).

Hanausek-Walaszek et al., Cancer Investigation, 2:443–441 (1984).

French et al., Cancer Letters, 23:45–52 (1984).

Schumm et al., Cancer Research, 44:4011–4406 (1984).

Walaszek et al., Cancer Letters, 20:277–282 (1983).

(List continued on next page.)

Primary Examiner—Christine M. Nucker
Assistant Examiner—M. P. Woodward
Attorney, Agent, or Firm—Arnold, White & Durkee

[57] ABSTRACT

A method is disclosed of adjunctive diagnostic testing and for monitoring the status of cancer treatment in an animal. The method includes the steps of (a) providing a sample of biological material from the animal; (b) contacting the sample with antibodies or other specific probes to a tumor-associated protein; and (c) determining the presence of an immunological reaction product formed by reaction between the antibodies (or other probes) and a protein present in the biological material, the presence of an immunological reaction product being indicative of the presence of cancer or likelihood of presence in the future of cancer. Also disclosed is a method of preparing monospecific antibodies to a protein which is particularly suited for very small quantities of rare proteins and for poorly antigenic proteins, where produced antibodies can suitably be used in the monitoring method or for other specific purposes, according to the selected protein. The method of preparing such antibodies involves immunizing an animal by implanting into the animal a section of a nitrocellulose blot, the section containing a selected protein.

11 Claims, 3 Drawing Sheets

U.S. PATENT DOCUMENTS

| | | | |
|---|---|---|---|
| 4,791,066 | 12/1988 | Ishiguro | 436/516 |
| 4,803,169 | 2/1989 | Linsley | 435/7 |
| 4,804,626 | 2/1989 | Bellet | 435/7 |
| 4,937,185 | 6/1990 | Webb et al. | 435/7 |

OTHER PUBLICATIONS

Schumm et al., Cancer Research, 42:4964–4969 (1982).
Cohn et al., Cancer Investigation, 4:305–327 (1986).
Guirguis et al., Journal of the National Cancer Institute, 80:1203–1211 (1988).
Waalkes, Laboratory Management, (Nov. 1985).
Lambert, British Journal of Obstetrics and Gynaecology, 94:193–195 (1987).
Couto, The Compendium on Continuing Education, 7:291–300 (1985).
Ferrer, JAVMA, 175:1281–1286 (1979).
Jeglum, JAVMA, 190:174–178 (1987).
Everman et al., Am. J. Vet. Res., 47:1885–1887 (1986).
Ennever et al., Discussions Forum, 73–78.
Troutman, JAVMA, 193:1056–1058 (1988).
Smith, Bio Essays, 3:225–229.
Hook, AMBIS Beta Scanning System TM Automated Microbiology Systems, Inc. San Diego, Calif.
Hanausek-Walaszek et al., Progress in Clinical and Biological Research, in press.
Hanausek-Walaszek et al., Cancer Letters, in press.
Hanausek-Walaszek et al., manuscript.
Hanausek-Walaszek et al., Proc. Am. Assoc. Cancer Res., vol. 30, abstract No. 754 at 190 (Mar., 1989).
Larroya et al., Proc. Am. Assoc. Cancer Res., vol. 30, abstract No. 1385 at 349 (Mar. 1989).
Hanausek et al., Proc. AACR, vol. 29, abstract No. 665 at 167 (Mar. 1988).
Coghlan et al., Subcutaneous Immunization of Rabbits Using Metro-cellulose Paper Strips Impregnated with Microgram Quantities of Protein, manuscript.
Hanausek et al., An Improved Procedure for Purification of a Canine p65 Tumor-Associated Protein and Antibodies Thereto, manuscript.
Coghlan, pre-proposal titled "Diagnostic and Premonitory Uses of a 65 KDa Tumor-Associated Protein in Canine Malignancy" (1989).

DIAGNOSTIC AND PREMONITORING USES OF A 65 KDA TUMOR-ASSOCIATED PROTEIN IN COMPANION AND DOMESTIC ANIMAL MALIGNANCY

This application is a continuation of application Ser. No. 07/460,045 filed Jan. 2, 1990, which is a continuation-in-part of U.S. Ser. No. 07/426,408, filed on Oct. 24, 1989, now pending, which is incorporated by reference in this application.

FIELD OF THE INVENTION

This invention relates to the use of a cancer-associated protein in differentiating malignant and non-malignant diseases, in gauging response to cancer therapy, and in monitoring continued regression of disease in treated companion or domestic animals to enable the prompt detection of disease recurrence and early therapy.

BACKGROUND OF THE INVENTION

In spite of improved treatments for certain forms of cancer, it is still a leading cause of death in the United States. This is true not only for humans, but also for domestic and companion animals such as dogs, cats, horses, and cattle. For example, millions of dollars are lost each year due to the forced slaughter of cattle that have lymphosarcoma. As another example, lymphosarcoma is the most common hematopoietic malignancy of dogs, with an incidence of about 0.1–0.3% in the general population. Without chemotherapy, canine lymphosarcoma runs a rapid course and is uniformly fatal.

In cases where the primary tumor in an animal has been substantially removed by surgery or destroyed by other means, it is important that the veterinarian or pathologist be capable of detecting any trace of cancer in the animal (either in the form of residues of the primary tumor or of secondary tumors caused by metastasis), in order that the veterinarian can prescribe appropriate subsequent treatment, such as chemotherapy. The quantities of cancer cells that must be detected for early diagnosis or following removal or destruction of the primary tumor are so small that the veterinarian or pathologist cannot rely upon physical examination of the cancer site. Moreover, in many cases the cancer site is of course not susceptible to direct visual observation, and it is not possible to predict exactly where cancer is likely to occur. In addition, even when tissue indicative of a malignancy can be visually detected, histologic differentiation of the malignancy can be difficult, even for experienced pathologists. Accordingly, sensitive tests have to rely upon detection of cancer-associated materials, usually proteins, present in body fluids of animals who have, or are about to develop, cancer cells in their bodies.

Several diagnostic materials for detection of cancer-associated proteins are available commercially. Tests for alpha-fetoprotein are used to detect primary liver cancer and teratocarcinoma in humans; carcinoembryonic antigen is used for digestive system cancers, as well as lung and breast carcinomas; chorionic gonadotropin is employed to detect trophoblast and germ cell cancers; calcitonin is used for thyroid gland cancers; and prostatic acid phosphatase is used to detect prostate carcinoma. These markers are detectable in advanced rather than in early cancer.

Unfortunately, many of the commercially available tests are only applicable to a narrow range of cancer types, and therefore these tests suffer not only from the disadvantage that other types of cancer may be missed but also from the disadvantage that the narrow applicability of the tests means that it may be necessary to run multiple tests on a single patient or animal for diagnostic purposes, a procedure which not only increases the expense of the diagnostic testing but also increases the risk that one or more of the tests may give a false positive result. Accordingly, there is a need for a single diagnostic test able to detect the presence of very small amounts of cells of a wide variety of different cancers. The ideal marker would be one that is specific and universal. Such a marker may exist if malignant transformation is associated with the expression of a unique gene product in all kinds of transformed cells.

It is already known that serum from the blood of animals suffering from a wide variety of cancers contains an oncofetal protein having a molecular weight of approximately 60,000 and having the capacity to increase the release of ribonucleic acid (RNA) from cell nuclei. This protein is referred to as oncofetal RNA-transport protein (ORTP) or 60 kDa tumor-associated protein.

ORTP is localized in the cytoplasm of tumors of humans and experimental animals and small amounts are released into the host circulatory system. The 60 kDa ORTP is notably absent from the nuclei of rat liver and rat liver tumors. It has been shown to be present in fetal rats at 18 days of gestation and in human and rat amniotic fluid, but not in maternal blood. It has not been detected in adult rats. Nor is it present in detectable concentrations in the blood of normal human subjects or those with a variety of non-neoplastic conditions or diseases, including benign tumors and other non-neoplastic proliferative diseases. In contrast, of more than 200 cancer patients with confirmed active disease, all tested positive for the factor. It was also present in all of about 200 tumor-bearing rats tested.

Unfortunately, antibodies to the rat 60 kDa cancer-associated protein preparation purified as described in the prior art do not cross-react with human or mouse ORTP. Thus, the 60 kDa cancer marker protein from different species are not immunologically equivalent, e.g., an antibody to the rat cancer marker protein does not cross-react with a human or mouse cancer marker protein. Thus, when the purified 60 kDa cancer marker protein preparation is to be used for production of antibodies for diagnostic purposes, it is probably necessary to begin the preparation process with plasma from the species in which the diagnosis is to be used.

Previous attempts to use RNA-transport-stimulating oncofetal proteins as markers to monitor the long-term effects of cancer treatment have not been successful. In particular, there has been a need for improved methods of monitoring the response of animals to treatment for cancer, in order to verify remission after treatment and to detect the onset of a recurrence of cancer.

We have now invented an improved method for monitoring the status of cancer treatment in animals, an improved adjunctive diagnostic test for malignancy in companion and domestic animals, and an improved method of preparing monospecific antibodies for use in the monitoring method.

SUMMARY OF THE INVENTION

The present invention concerns a method of monitoring the status of cancer treatment in an animal, including the steps of (a) providing a sample of biological material from an animal which has undergone therapy for cancer; (b) contacting the sample with a specific probe, such as one comprising antibodies, to a tumor-associated protein; and (c) determining the presence of an immunological reaction product formed by reaction between the probe and a protein present in the biological material, the presence of an immunological reaction product being indicative of the presence of cancer or likelihood of presence in the future of cancer. The presence of the immunological reaction product can be determined, for example, by radioimmunoassay, enzyme linked immunosorbent assay, or immunohistochemical staining.

Similarly, in a method of diagnosing cancer in a companion or domestic animal, the same steps would be performed, beginning with a sample of biological material from a companion or domestic animal that is suspected of having a cancerous condition.

In a particular embodiment, the presence of the immunological reaction product is determined by (a) fractionating the sample of biological material to separate the protein components thereof; (b) radiolabelling the fraction of the sample that contains the tumor-associated protein by contacting the sample with radiolabelled antibody which is specific for the tumor-associated protein; (c) scanning the radiolabelled sample with apparatus which can detect the pattern of radioactive material present in the sample; and (d) comparing the results of the scanning to a standard. The biological material can suitably be plasma, urine, serum, cytosol fluid, ascites, or tissue.

The present invention also concerns a method of preparing monospecific antibodies to a protein, including the steps of (a) immunizing an animal by implanting into the animal an implant material selected from the group consisting of nitrocellulose and a section of a nitrocellulose blot, the implant containing a selected protein; (b) collecting blood from the animal after sufficient time has passed to allow antibodies to the implanted protein to be formed; and (c) detecting and collecting the antibodies in the blood which are specific to the proteins.

In one aspect, the invention employs a protein preparation comprising a cancer-associated protein having the following characteristics:

(a) not being precipitated by 30% saturated aqueous ammonium sulfate solution at 25° C.;

(b) molecular weight ca. 65,000±5,000, with some species variation, as measured by electrophoresis on 10% SDS polyacrylamide slab gels;

(c) binds completely to a phenyl hydrophobic interaction column in a buffer containing 20% ammonium sulfate in 50 mM TrisCl, pH 7.5 with 1 mM EDTA and 10 mM 2-mercaptoethanol and is eluted by gradient when the ammonium sulfate concentration drops to ca. 16%;

(d) exhibiting interspecies immunological cross-reactivity, specifically the canine p65 reacts with antibodies raised in rabbits directed against the rat p65 protein;

(e) present in only some lesions characterized by altered enzyme expression (i.e., those assumed to be precursors of malignant tumors) and presumably all malignant tumors but substantially absent from normal tissue, specifically absent from the maternal blood of non-cancerous normal mammals;

(f) localized primarily in the nuclear envelopes (but not within the nucleoli or intranuclear structures) with only small amounts present in the cytoplasm from where it is released to the blood circulation in vivo or cell culture medium in vitro;

(g) induced in normal, adult tissues by chemical carcinogens (initiators) but not by tumor promoters, the carcinogen induced production being enhanced by the latter; and (h) having an RNA-releasing activity of at least about 10.0 units per milligram of total protein when assayed by the procedure set forth in column 4 of the U.S. Pat. No. 4,746,539.

This cancer-associated protein is described and claimed in U.S. patent application Ser. No. 426,408, filed on Oct. 24, 1989, titled "Tumor Marker Protein and Antibodies Thereto for Cancer Risk Assessment or Diagnosis," naming Margaret Hanausek-Walaszek, Thomas J. Slaga, and Zbigniew Walaszek as inventors. That patent application is incorporated herein by reference.

As used herein, the term "substantially" is a relative term meaning largely but not absolutely wholly as specified. The term allows for trace deviance from the absolute.

The monitoring method of the present invention is useful for differential diagnosis of malignancy, for confirming remission after treatment for cancer, and for monitoring continued recovery. The present invention's sensitivity allows it to detect impending relapse before tumor mass could be detected. Therefore, it is preferred to take a sample from an animal periodically after the animal has completed cancer treatment, and analyze these periodic samples as described herein.

The present invention is useful in both the companion animal and agricultural animal sectors. The monitoring method could be performed in a laboratory, with treating veterinarians forwarding samples from the affected animals to the laboratory for analysis. Alternatively, a kit could be prepared, containing the necessary reagents, for use by the treating veterinarian.

The speed of diagnosis and the utility of the results are enhanced by the use of a computer to store and analyze the results. For example, a computer-based system allows the results of one test to be quickly compared to a standard which is already stored in memory. This approach also increases accuracy and reproduceability.

BRIEF DESCRIPTION OF THE DRAWINGS

FIG. 3 shows immunoblot analysis of serum from a normal dog (1), dogs with diagnosed lymphosarcoma (2–5), tissue culture medium (6), and this same medium in which dog lymphosarcoma cells were grown (7). Monospecific anti-dog p65 antibodies raised in rabbits were used to detect the presence of p65.

DETAILED DESCRIPTION OF SPECIFIC EMBODIMENTS

Figure 1A:
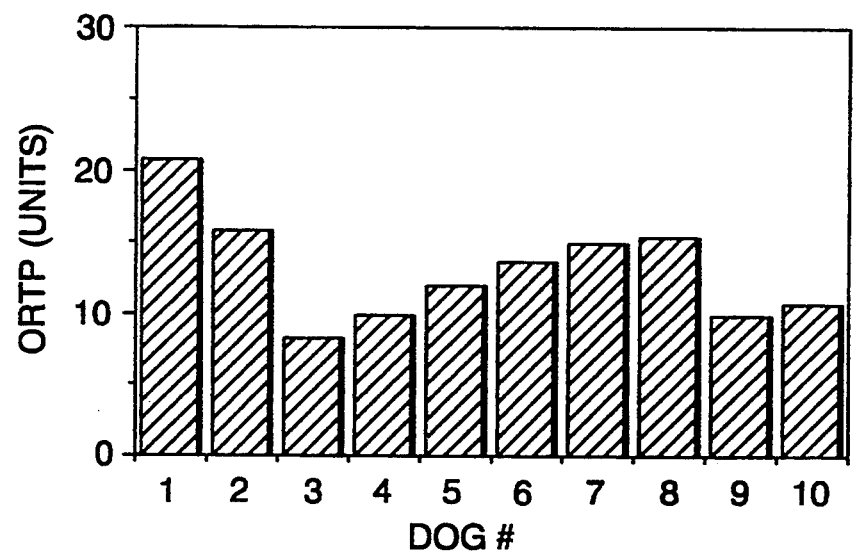
FIG. 1 shows the plasma levels of the 65 kDa cancer-associated protein (p65) in dogs with (A) and without (B) lymphosarcoma.

Method for Adjunctive Diagnostic Testing, or Monitoring Remission or Recurrence of Cancer After Treatment Samples of blood plasma, urine, serum, or tissue are obtained from animals at selected intervals upon presentation and/or after treatment for cancer (e.g., after surgical resection of a tumor, or after chemotherapy or radiation treatment).

Briefly, samples of the blood plasma, urine, serum, or tissue containing the same amount of total protein are mixed with an electrophoresis sample buffer, boiled for three minutes and subjected to 12.5% SDS-PAGE. Subsequently, the gel slabs are prepared for transfer by equilibrating for one hour in 0.025 M Tris, 0.192 M glycine, 20% (v/v) methanol, pH 8.3, and then transblotted onto nitrocellulose sheets. Improvements in more gentle sample preparation may enhance the overall assay. To conduct the immunoassay, the nitrocellulose sheets are treated with appropriate blocking solution to block unspecific binding sites and incubated overnight, either with pre-immune serum (controls) or antibody against the p65 protein diluted 1:200. Secondary biotinylated antibody is applied next and the color is developed using ABC Elite Kit from Vector Laboratories, Burlingame, Calif. The highly specific polyclonal antibody against p65 is obtained by immunizing rabbits with pure canine or rat p65 preparations. As an alternative, mouse monoclonal antibodies to p65 may be prepared using the techniques generally described in "Hybridoma Techniques" Cold Spring Harbor, N.Y., 1980, ISBN 0-87969-143-3. As an additional alternative, commercial RNA probes (radiolabelled with $p^{32}$) or cDNA probes could be used.

The immunoblots are photographed and the bands of p65 immune complexes on the film are quantitated using a laser densitometer coupled to an integrator. Alternatively, following probing with the antibodies to p65 or pre-immune serum, nitrocellulose sheets are labeled with $^{125}I$-protein A, or alternatively with a cDNA or RNA probe. The labeled sheets are subjected to autoradiography followed by scanning the film with a laser densitometer coupled to an integrator. Another alternative is to use an ELISA procedure.

To interpret the plasma or serum or tissue samples, the relative quantity of p65 in the sample is indicated by the intensity of a band at nominal molecular weight about 65,000 as measured by laser scanning. Comparison with the corresponding area of the control (derived with the use of pre-immune serum) permits distinguishing response specific for p65 above non-specific background response. Specific activity of the marker band from clinical samples taken after treatment is compared with the samples taken prior to treatment and/or with the average sample from a normal healthy pool. The clinical response can be then expressed as a factor against the response prior to treatment or against the response of the normal healthy pool. Steady increases in the value of clinical response over a period of time are indicative of an increased risk of cancer relapse or treatment failure. A high initial response is indicative of an existing cancer.

The following examples provide details of various specific embodiments of the present invention.

EXAMPLE 1

This example illustrates the methods of the present invention for purification of the p65 tumor-associated protein and preparation of antibodies thereto.

Purification of Canine p65 Protein

Preparation of the antibody involves purification of the canine p65 marker protein from the blood plasma of tumor-bearing dogs. Specifically, the blood plasma was obtained from dogs with diagnosed lymphosarcoma and fractionated with ammonium sulfate. The protein precipitating between 30% and 60% of aqueous ammonium sulfate solution was collected by 30 min.-centrifugation at 10,000×g, dissolved in a small volume of 50 mM Tris-Cl buffer pH 7.5, with 50 mM NaCl, 10 mM 2-mercaptoethanol and 1 mM EDTA, and dialyzed overnight against the same buffer. After dialysis, proteins were loaded on a LKB TSK 3000 SW molecular sieving column and separated according to the molecular weight using a LKB HPLC system. Fractions containing proteins with molecular weight in the range of 50–90 kDa were collected and dialyzed overnight against buffer A, containing 20% ammonium sulfate in 50 mM Tris-Cl, pH 7.5 with 10 mM 2-mercaptoethanol and 1 mM EDTA.

Following dialysis, the 50–90 kDa proteins were loaded on a phenyl hydrophobic interaction column (PHI) (LKB, Pharmacia) equilibrated with buffer A. The p65 marker protein weakly binds to the PHI column and is eluted in the first distinct peak by a gradient of 80% to 0% of buffer A, in combination with buffer B (50 mM Tris-Cl, pH 7.5 with 10 mM 2-mercaptoethanol and 1 mM EDTA, supplemented with 50% ethylene glycol). Fractions containing the p65 marker protein are then combined and dialyzed against buffer A devoid of ammonium sulfate, concentrated by lyophilization and electrophoresed on 12.5% SDS-PAGE at constant current of a 10 mA for 2 hours at room temperature. Proteins are transblotted to a $0.22\mu$ nitrocellulose sheet as described by Towbin et al., *Proc. Natl. Acad. Sci. U.S.A.*, Vol. 76, pp. 4350–4353 (1979). A reversible Ponceau A stain was used to visualize the nitrocellulose bound proteins according to the procedure of Salinovich and Montellaro, *Anal. Biochem.*, Vol. 156, pp. 341–347 (1986). The band of the p65 protein was cut out of the nitrocellulose sheets and used for immunization of rabbits.

Preparation of Antibodies to p65

The canine p65 protein was labeled in vitro by $^{32}P$ phosphorylation according to the method of Rose et al., *J. Biol. Chem.* 256, 7468–7477 (1981). To measure the release of an antigen from a nitrocellulose strip, 25 micrograms of $^{32}P$ labeled antigen was transblotted onto $0.22\mu$ nitrocellulose sheet. The radioactivity of bound antigen was determined, and after washing the strips in Tris-buffered saline, pH 7.5, release of radioactivity was determined every 24 hours. Adjustment for natural decay was made.

Specific Pathogen Free (Pasteurella) male New Zealand White rabbits of approximately four kilograms body weight were used for the study (Myrtle's Rabbitry). The rabbits were singly housed in stainless steel rabbit cages in an AAALAC-accredited animal facility in accordance with federal laws and guidelines. Feed (High-Fiber Rabbit Chow, Purina) and water were provided ad libitum. Preimmune (day 0) and test blood samples (10 days following each of four immunizations on day 1, 14, 28, and 42) were obtained from the central artery of the ear or a lateral ear vein.

Prior to administering anesthesia for the implant procedure, food was withheld overnight. The rabbits were injected with a combination of xylazine (Haver-Lockhart), 3.0 pk mg/kg. I.M. followed five minutes later with ketamine (Bristol), 25 mg/kg. I.M. The anesthetized rabbits were then placed in sternal recumbency, the dorsal fur was removed with surgical clippers, and the surgical site was aseptically prepared with provodine-iodine (Wescodyne, West Chemical) followed by 70% ethanol.

Six incisions about 1.0 cm each were made in an anterio-posterior direction through the skin and subcutis with a scalpel. The incisions were undermined with blunt and sharp dissection to allow implant placement over the superficial epaxial musculature. The nitrocellulose strip was cut into six pieces (each approx. 0.5 cm×1.5 cm) which were then formed into rolls for insertion. Following placement, the skin edges were opposed with tissue forceps and closed with surgical adhesive (Vetbond, 3M). Adequate spacing (about 2.5 cm) between insertion fields will allow subsequent immunization incisions to be made adjacently. Terminal blood collection was made in Alsever's solution in anesthetized rabbits by the use of a vacuum assisted collection device (Foytik et al., in press) which maximizes recoverable blood volume.

ELISA Assay

An ELISA assay or immunoblotting analyses were conducted to determine the potency and specificity of the antisera obtained.

A standard ELISA procedure was used for detection of specific antibodies in serum. 96 well microtiter plates designed for ELISA were used (Immunol 2, Dynatech). For detection of rabbit anti-canine-p65 antibodies, the ELISA plates were pre-coated with several different concentrations of antigen. To test sera, a positive reference serum and a negative pre-immune serum were added to the wells in five-fold dilutions in PBS. Anti-p65 antibodies were detected by goat anti-rabbit IgG conjugated with horse radish peroxidase (Bio-Rad). After the substrate reaction, plates were read on an ELISA plate reader at 405 nm (Litton Bionetics, Laboratory Product Division, S.C.). A serum sample was considered positive when it read 0.05 units or more above the background. The results of ELISA serum titer determinations in rabbits inoculated as described above is shown in Table 1.

TABLE 1

Appearance of serum antibodies in rabbits after subcutaneous immunization with nitrocellulose strips loaded with canine tumor-associated antigen p65.

| Treatment | Number of Immunizations | | | |
|---|---|---|---|---|
| 25 μg of p65-NC | 1 | 2 | 3 | 4 |
| Total μg of p65 | 25 | 50 | 75 | 100 |
| Number of positive rabbits | 0/2 | 2/2 | 2/2 | 2/2 |
| Anti-p65 antibody titer | 0 | 100 | 400 | 1000 |
| Preimmune serum | 0 | 0 | 0 | 0 |
| Sham control non-antigen NC immunization | 0 | 0 | 0 | 0 |

Probing of Western blots with prepared antibody was carried out as follows. The purified canine tumor-associated protein, p65, was separated by PAGE and electrophoretically transferred to nitrocellulose as described above. Free binding sites on the nitrocellulose sheets were then blocked overnight using 1% normal goat serum in TTBS buffer (0.5% Tween, 0.1 mM Tris-HCl, pH 7.1, 0.9% saline). Antisera obtained from immunized rabbits were diluted serially in the blot buffer (TTBS) and incubated with the nitrocellulose strips for one hour at room temperature. The blots were then washed with several changes of TTBS buffer containing 1% goat serum. Bound antibody was detected using biotinylated second antibody (goat anti-rabbit IgG, biotinylated) and the avidin-biotin-peroxidase method (Vectastain ABC Elite, Vector, Burlingame, Calif.). To develop blots, 0.02% hydrogen peroxide was used, mixed with 0.1% diaminobenzidine tetrachloride (DAB) made in 0.1 M Tris-HCl buffer, pH 7.2. Color generally developed within five to ten minutes; blots were rinsed with distilled water and air dried to preserve color. Alternatively, bound antibody was detected by incubating the nitrocellulose strips with $^{125}$I-Protein A ($1 \times 10^6$ cpm/ml of blot buffer). After a 60 min. incubation, unbound label was removed by repeated washes of the blots with PBS buffer containing 0.5% Tween. The bound antigen $^{125}$I-Protein A complex was detected by overnight autoradiography using Kodak X-OMAT-AR film.

Alternatively, an imaging instrument can be used to record the decaying beta particles of $^{125}$I. One such unit, the Ambis Radioanalytic Imaging system (Automated Microbiology Systems Inc., San Diego, Calif.), employs an IBM AT computer to record the image produced by isotope decay. This image is accessed via software commands, and can be manipulated for analysis using its video image. Points of particle activity show as bright spots that build up to form a banding pattern—very similar to that seen on a conventionally stained gel. The Ambis detector employs a moving stage that the blot or gel is dry mounted to and is covered by thin mylar film. The detector head moves over the blot picking up particle emissions, recording each position, and counts detected at that position. Once the scan is complete (scans up to 5000/min. possible), it is stored and can be recalled for analysis and printing. Once stored in memory, the blot can be discarded since the scan itself yields the actual counts at each position. Using a grid function in the software, it is possible to extract the counts for a specific protein band at any place on the blot.

These quantitative data values can be compared directly to control samples run on the same protocol, and actual values of p65 can be recorded. These values, lower or higher than the controls, can be used in clinical decisions regarding disease progress or remission. Unlike other protein detection methods, this protocol allows direct visualization and direct quantitation of points of activity. The Ambis system is easy to use and will give scan results in as little as 15 minutes. Should modifications to the gels, blots, ligand used, etc. be changed for greater resolution or clarity, this step of the detection scheme will not need changing. This detector can accept any type of relatively flat sample up to 20 cm square in size with other isotopes imaging as well or better than the $^{125}$I used now. Another advantage to use of this imaging scheme is that the blot or gel can be used for other purposes once the scan is obtained. This could prove valuable with very small amounts of sample or if further testing is needed.

EXAMPLE 2

Figure 1B:
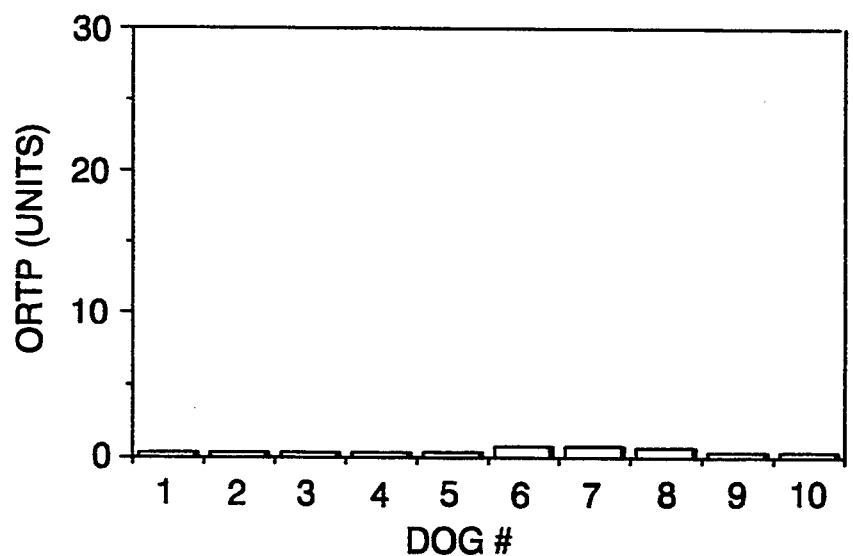

An RNA-transport assay for p65 was used to screen a number of dogs with and without lymphosarcoma. FIG. 1 shows the results of screening 20 animals, 10 dogs each in an experimental group (A) and a control group (B). The significantly higher level ($p<0.01$) of plasma p65 was consistently observed in dogs with lymphosarcoma (group A), as compared with the healthy controls (group B).

Figure 2A:
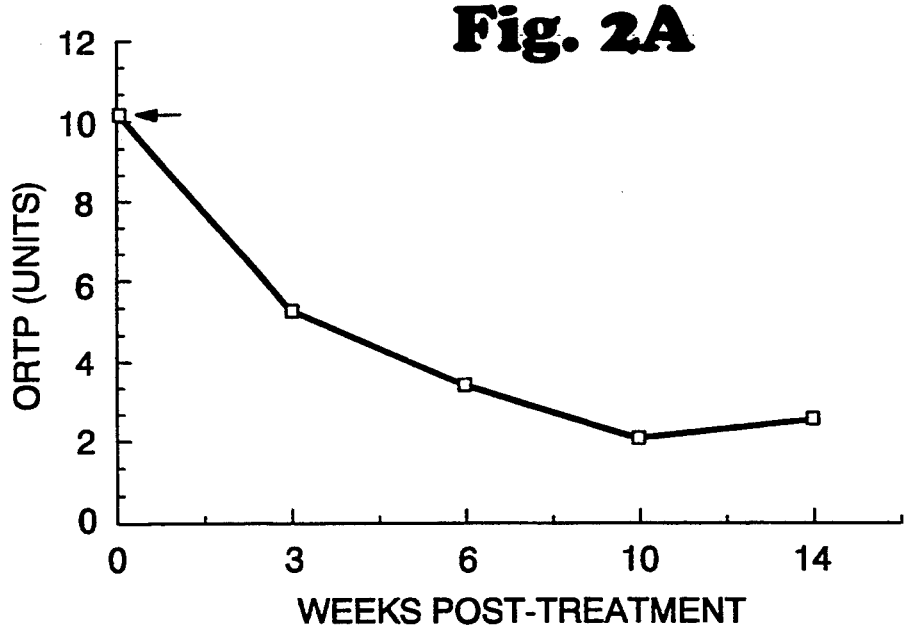
FIG. 2 shows the plasma levels of p65 in two different dogs (A and B) with lymphosarcoma that were treated with one (A) or two (B) doses of adriamycin (36–38 mg/m² each).
Figure 2B:
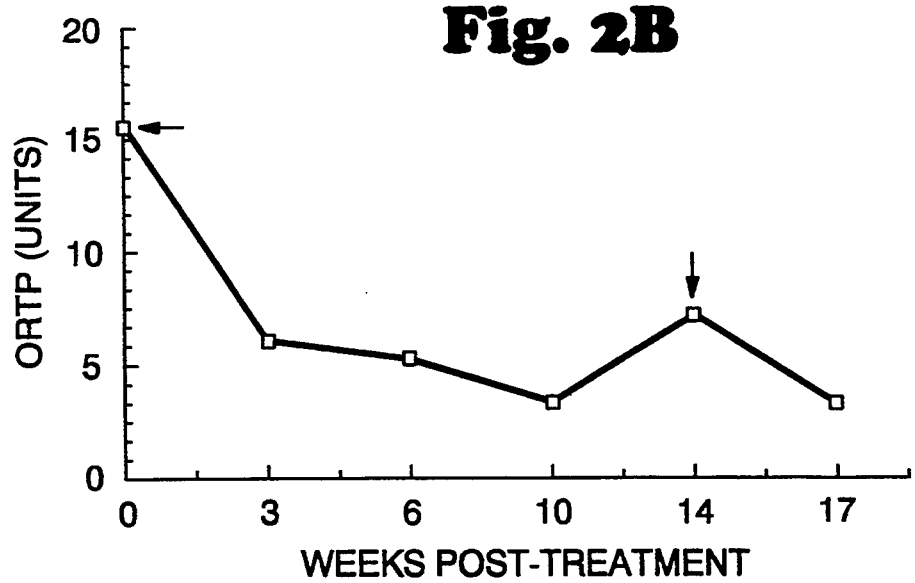

The RNA transport assay for p65 was then used to monitor the progress of chemotherapy of the canine lymphosarcoma. As shown in FIG. 2, p65 levels continued to decrease following one (A) or two doses (B) of adriamycin (36–38 mg/m² each). As shown in FIG. 2B, the use of the p65 marker enabled early detection of recurrence of the disease and intervention with the second dose (arrow) of the chemotherapeutic agent.

Figure 3:
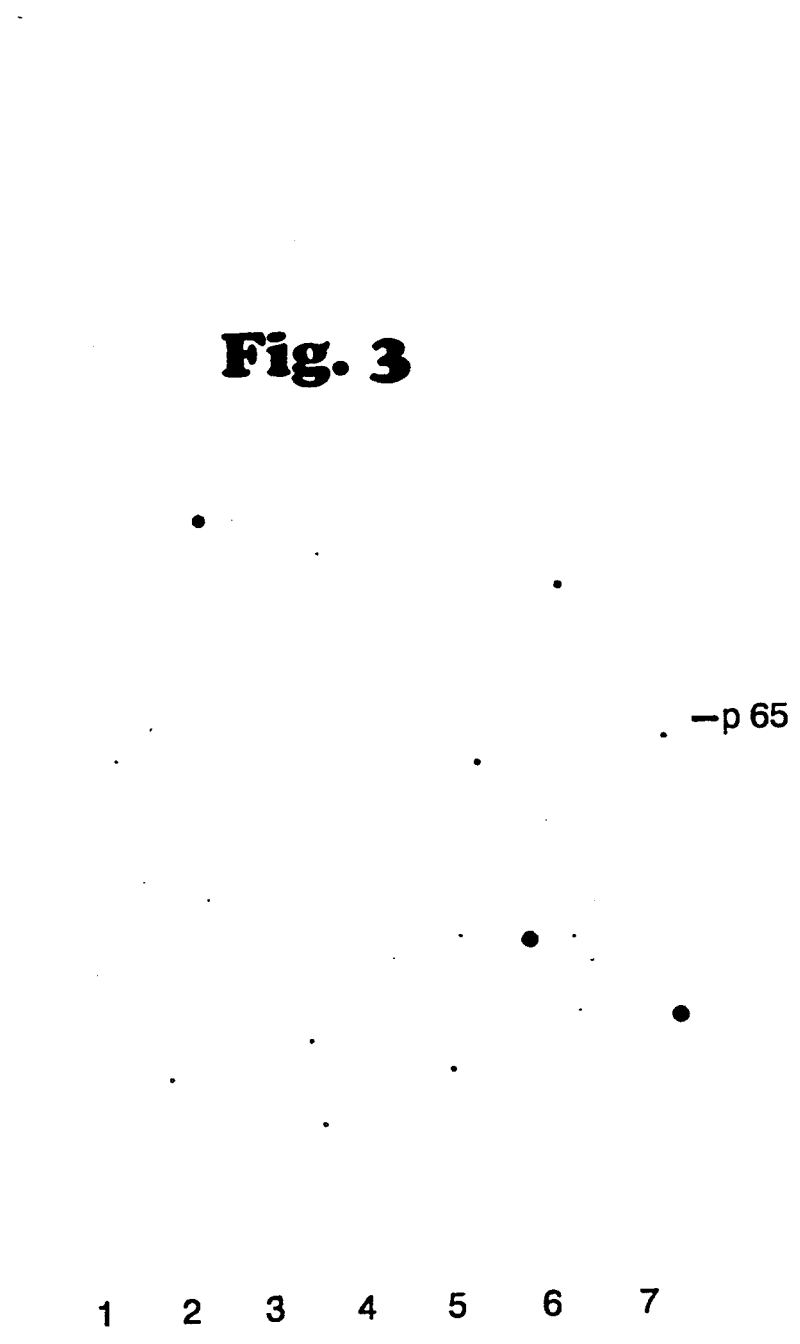

Serum from normal dogs or dogs with lymphosarcomas and cell culture media were analyzed on blots by incubating the nitrocellulose strips with $^{125}$I-Protein A ($1 \times 10^6$ cpm/ml of blot buffer). The bound p65—$^{125}$I—Protein A complexes were detected by overnight autoradiography using Kodak X-OMAT-AR films. As shown in FIG. 3, immunoblotting analysis of serum or cell culture medium allows for quick screening for the presence of p65 cancer-associated marker protein and subsequent analysis using rabbit anti-canine p65 antibody.

The preceding description of specific embodiments of the invention is intended to illustrate the invention, not to provide an exhaustive list of all possible embodiments. Those skilled in the art will recognize that changes can be made to the specific embodiments described above which would remain within the scope of the invention.

We claim:

1. (amended) A method of monitoring the status of cancer treatment in a mammal, including the steps of:
   providing a sample of biological material from mammal which has undergone therapy for cancer;
   contacting the sample with antibodies specific for an immunogen of a 65 kD tumor-associated protein, the immunogen being prepared by the process comprising the steps of:
   (a) collecting from plasma, tumor cytosol or ascitic fluid of carcinoma-bearing mammals or from culture medium in which cancer cells were grown, the protein fraction which is precipitated from plasma, tumor, cytosol or ascitic fluid between 30% and 60% saturation of an aqueous ammonium sulfate solution or from culture medium at 90% saturation of an aqueous ammonium sulfate solution, respectively;
   (b) chromatographing the protein fraction on a molecular sieving column and collecting a protein fraction having a molecular weight in the range of about 50 to 90 kilodaltons;
   (c) applying the collected chromatographed protein fraction to a high performance liquid chromatography (HPLC) phenyl hydrophobic interaction column and allowing protein to bind to the column;
   (d) eluting the bound protein on the phenyl hydrophobic interaction column with a buffer comprising about 16% ammonium sulfate;
   (e) collecting the first distinct protein peak eluted from the column;
   (f) electrophoresing the collected protein;
   (g) transblotting the electrophoresed protein to a nitro-cellulose sheet; and
   (h) cutting from the nitro-cellulose sheet that portion which contains a band of protein corresponding to about 65 kD; and
   determining the presence of an immunological reaction product formed by reaction between the antibodies and the 65 kD tumor-associated protein, the presence of an immunological reaction product being indicative of the presence of cancer.

2. The method of claim 1, where the presence of the immunological reaction product is determined by radioimmunoassay, enzyme linked immunosorbent assay, or immunohistochemical staining.

3. The method of claim 1, where the biological material is selected from the group consisting of plasma, urine, serum, cytosol fluid, ascites, or tissue.

4. The method of claim 1, where the presence of the immunological reaction product is determined by:
   fractionating the sample of biological material to separate the protein components thereof;
   contacting the fraction of the sample that contains the tumor-associated protein with radiolabeled antibodies which are specific for the tumor-associated protein;
   scanning the fraction of the sample that contains the tumor-associated protein with apparatus which can detect the pattern of radioactive material present in the fraction; and
   comparing the results of the scanning to a standard.

5. The method of claim 4, where the pattern of radioactive material that is detected is stored in a computer memory.

6. A method of diagnosing cancer in companion and domestic mammals, including the steps of:
   providing a sample of biological material from a companion or domestic mammal which is suspected of having a neoplastic condition;
   contacting the sample with antibodies specific for an immunoqen of a 65 kD tumor-associated protein, the immunogen being prepared by the process comprising the steps of:
   (a) collecting from plasma, tumor cytosol or ascitic fluid of carcinoma-bearing mammals or from culture medium in which cancer cells were grown, the protein fraction which is precipitated from plasma, tumor, cytosol or ascitic fluid between 30% and 60% saturation of an aqueous ammonium sulfate solution or from culture medium at 90% saturation of an aqueous ammonium sulfate solution, respectively;
   (b) chromatographing the protein fraction on a molecular sieving column and collecting a protein fraction having a molecular weight in the range of about 50 to 90 kilodaltons;
   (c) applying the collected chromatographed protein fraction to a high performance liquid chromatography (HPLC) phenyl hydrophobic interaction column and allowing protein to bind to the column;
   (d) eluting the bound protein on the phenyl hydrophobic interaction column with a buffer comprising about 16% ammonium sulfate;
   (e) collecting the first distinct protein peak eluted from the column;
   (f) electrophoresing the collected protein;

(g) transblotting the electrophoresed protein to a nitro-cellulose sheet; and (h) cutting from the nitro-cellulose sheet that portion which contains a band of protein corresponding to about 65 kD; and determmning the presence of an immunological reaction product formed by reaction between the antibodies and the 65 kD tumor-associated protein, the presence of an immunological reaction product being indicative of the presence of cancer.

7. The method of claim 6, where the presence of the immunological reaction product is determined by radioimmunoassay, enzyme linked immunosorbent assay, or immunohistochemical staining.

8. The method of claim 6, where the biological material is selected from the group consisting of plasma, urine, serum, cytosol fluid, ascites, or tissue.

9. The method of claim 6, where the presence of the immunological reaction product is determined by:

fractionating the sample of biological material to separate the protein components thereof;

contacting the fraction of the sample that contains the tumor-associated protein with radiolabeled antibodies which are specific for the tumor-associated protein;

scanning the fraction of the sample that contains the tumor-associated protein with apparatus which can detect the pattern of radioactive material present in the fraction; and comparing the results of the scanning to a standard.

10. The method of claim 9, where the pattern of radioactive material that is detected is stored in a computer memory.

11. A diagnostic kit, including:

antibodies specific for an immunogen of a 65 kD tumor-associated protein, the immunogen being prepared by the process comprising the steps of:

(a) collecting from plasma, tumor cytosol or ascitic fluid of carcinoma-bearing mammals or from culture medium in which cancer cells were grown, the protein fraction which is precipitated from plasma, tumor, cytosol or ascitic fluid between 30% and 60% saturation of an aqueous ammonium sulfate solution or from culture medium at 90% saturation of an aqueous ammonium sulfate solution, respectively;

(b) chromatographing the protein fraction on a molecular sieving column and collecting a protein fraction having a molecular weight in the range of about 50 to 90 kilodaltons;

(c) applying the collected chromatographed protein fraction to a high performance liquid chromatography (HPLC) phenyl hydrophobic interaction column and allowing protein to bind to the column;

(d) eluting the bound protein on the phenyl hydrophobic interaction column with a buffer comprising about 16% ammonium sulfate;

(e) collecting the first distinct protein peak eluted from the column;

(f) electrophoresing the collected protein;

(g) transblotting the electrophoresed protein to a nitro-cellulose sheet; and (h) cutting from the nitro-cellulose sheet that portion which contains a band of protein corresponding to about 65 kD;

the antibodies being capable of forming a immunological reaction product when contacted with the tumor-associated protein; and reagents for detecting the immunological reaction product by a method selected from the group consisting of radioimmunoassay, enzyme linked immunosorbent assay, and immunohistochemical staining.

* * * * *

UNITED STATES PATENT AND TRADEMARK OFFICE
CERTIFICATE OF CORRECTION

PATENT NO. : 5,411,868
APPLICATION NO. : 08/021738
DATED : May 2, 1995
INVENTOR(S) : Margaret Hanausek-Walaszek et al.

Page 1 of 1

It is certified that error appears in the above-identified patent and that said Letters Patent is hereby corrected as shown below:

In column 1, line 12, please insert --This invention was made with government support under CA054296 and RR005511 awarded by the National Institutes of Health. The government has certain rights in the invention.--.

Signed and Sealed this

Twenty-fifth Day of March, 2008

JON W. DUDAS
*Director of the United States Patent and Trademark Office*